United States Patent [19]

de Costa et al.

[11] Patent Number: 5,130,330
[45] Date of Patent: Jul. 14, 1992

[54] NITROGEN-CONTAINING CYCLOHETERO CYCLOALKYLAMINOARYL DERIVATIVES FOR CNS DISORDERS

[75] Inventors: Brian R. de Costa, Gaithersburg; Kenner C. Rice, Bethesda, both of Md.; Nancy M. Gray, Ellisville; Patricia C. Contreras, Ballwin, both of Mo.; Arthur E. Jacobson, Potomac, Md.; Andrew Thurkauf, Branford, Conn.; Lilian A. Radesca, Brookeville, Md.; Wayne D. Bowen, East Providence, R.I.

[73] Assignee: G. D. Searle & Co., Chicago, Ill.

[21] Appl. No.: 473,008

[22] Filed: Jan. 31, 1990

[51] Int. Cl.$^5$ ............... A61K 31/40; C07D 295/073
[52] U.S. Cl. ..................................... 514/429; 548/578
[58] Field of Search ........................ 558/578; 514/429

[56] References Cited

U.S. PATENT DOCUMENTS

| | | | |
|---|---|---|---|
| 4,204,003 | 5/1980 | Szmuszkovicz | 560/27 X |
| 4,460,600 | 7/1984 | Kaplan et al. | 548/578 X |
| 4,463,013 | 7/1984 | Collins et al. | 548/407 X |
| 4,466,977 | 8/1984 | McMillan et al. | 548/578 X |
| 4,801,604 | 1/1989 | Von Voigtlander et al. | 514/429 |
| 4,855,316 | 8/1989 | Horwell et al. | 514/429 X |
| 4,876,269 | 10/1989 | Pennev et al. | 548/578 X |
| 4,891,382 | 1/1990 | Lancaster et al. | 514/429 |

OTHER PUBLICATIONS

S. M. Rothman and J. W. Olney, "Glutamate and the Pathophysiology of Hypoxia—Ischemic Brain Damage," *Annals of Neurology*, vol. 19, No. 2 (1986).
C. Carter et al, *J. Pharm. Exp. Ther.*, 247, (3), 1222–1232 (1988).
A. F. Gilman et al, *The Pharmacological Basis of Therapeutics*, 7th Edn., p. 404, MacMillan (1985).
C. G. Parsons et al, *Neuropharm.*, 25(2), 217–220 (1986).
W. Lason et al, *Brain Res.*, 482, 333–339 (1989).

B. R. de Costa et al, *J. Med. Chem.*, 32(8), 1996–2002 (1989).

*Primary Examiner*—Joseph Paul Brust
*Attorney, Agent, or Firm*—J. Timothy Keane; Charles E. Smith; Paul D. Matukaitis

[57] ABSTRACT

Certain nitrogen-containing cyclohetero cycloalkylaminoaryl compounds are described for treatment of CNS disorders such as cerebral ischemia, psychotic disorders and convulsions. Compounds of particular interest are of the formula

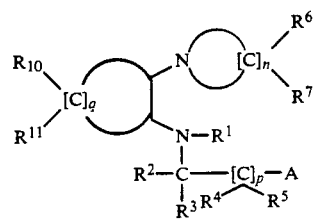

wherein $R^1$ is selected from hydrido, loweralkyl, cycloalkylalkyl of four to six carbon atoms, and loweralkenylloweralkyl; wherein each of $R^2$ and $R^3$ is independently selected from hydrido and loweralkyl; wherein each of $R^4$ through $R^7$, $R^{10}$ and $R^{11}$ is independently selected from hydrido, hydroxy, loweralkyl, benzyl, phenoxy, benzyloxy and haloloweralkyl; wherein n is a number selected from four through six; wherein p is a number selected from zero through four; wherein q is a number selected from three through five; wherein A is selected from phenyl, naphthyl and thienyl; wherein any of the foregoing A groups can be further substituted with one or more substituents independently selected from hydrido, hydroxy, loweralkyl, loweralkoxy, halo, haloloweralkyl, amino, monoloweralkylamino and diloweralkylamino; or a pharmaceutically acceptable salt thereof.

3 Claims, No Drawings

NITROGEN-CONTAINING CYCLOHETERO CYCLOALKYLAMINOARYL DERIVATIVES FOR CNS DISORDERS

FIELD OF THE INVENTION

This invention is in the field of clinical neurology and relates specifically to a class of therapeutically useful compounds, compositions and methods for treatment of Central Nervous System (CNS) dysfunctions, neurotoxic damage, or neurodegenerative diseases. For example, these compounds are particularly useful for treating neurotoxic injury which follows periods of hypoxia, anoxia or ischemia associated with stroke, cardiac arrest or perinatal asphyxia. These compounds are also useful as antipsychotics and anticonvulsives.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman and J. W. Olney, "Glutamate and the Pathophysiology of Hypoxia - Ischemic Brain Damage," *Annals of Neurology*, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS).

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with hypoxia, anoxia, or ischemia caused by stroke, cardiac arrest or perinatal asphyxia.

It is known that compounds of various structures, such aminophosphonovalerate derivatives and piperidine dicarboxylate derivatives, may act as competitive antagonists at the NMDA receptor. Certain piperidineethanol derivatives, such as ifenprodil and 1-(4-chlorophenyl)-2-[1-(4-fluorophenyl) piperidinyl]ethanol, which are known antiischemic agents, have been found to be non-competitive NMDA receptor antagonists [C. Carter et al, *J. Pharm Exp. Ther.*, 247(3), 1222–1232 (1988)].

There are many classes of compounds known for treatment of psychotic disorders. For example, current therapeutic treatments for psychoses use compounds classifiable as phenothiazine-thioxanthenes, as phenylbutylpiperidines and also as certain alkaloids. An example of a phenylbutylpiperidine compound of current use in psychotic treatment therapy is haloperidol [A. F. Gilman et al, *The Pharmacological Basis of Therapeutics*, 7th Edn., P. 404, MacMillan (1985)].

Certain nitrogen-containing cyclohetero cycloalkylaminoaryl compounds are known for pharmaceutical purposes. For example, U.S. Pat. No. 4,204,003 to Szmuszkovicz describes N-(2-aminocyclopentyl)-N-alkanoylanilides as antidepressant agents.

Certain aminocycloaliphatic benzamides have been described for various uses. For example, U.S. Pat. No. 4,463,013 to Collins et al describes aminocyclohexylbenzamides for use as diuretic agents. The compound (±)-trans-3,4-dichloro-N-methyl-N-[2-(1-pyrrolidinyl)-cyclohexyl]benzeneacetamide has been evaluated for its selectivity as an amino acid antagonist [C. G. Parsons et al, Neuropharm., 25 (2), 217–220 (1986)]. This same compound has been evaluated for its neuroprotective activity against kainate-induced toxicity [W. Lason et al, Brain Res., 482, 333–339 (1989)]. U.S. Pat. No. 4,801,604 to Vonvoightlander et al describes certain cis-N-(2aminocycloaliphatic)benzamides as anticonvulsants including, specifically, the compound cis-3,4-dichloro-N-methyl-N-[2-(1-pyrrolidinyl)cyclohexyl]-benzamide. These benzeneacetamide derivatives, such as trans-3,4-dichloro-N-methyl-N-[2-(1-pyrrolidinyl)cyclohexyl]benzeneacetamide, have been described as a highly selective ligand for kappa opioid receptors. Such kappa opioid affinity is believed associated with blockade of convulsions and protection from cerebral ischemia [B. R. de Costa et al, *J. Med. Chem.*, 32 (8), 1996–2002 (1989)].

Treatment of CNS disorders and diseases such as cerebral ischemia, psychotic disorders and convulsions, as well as prevention of neurotoxic damage and neurodegenerative diseases, may be accomplished by administration of a therapeutically-effective amount of a compound of the Formula I:

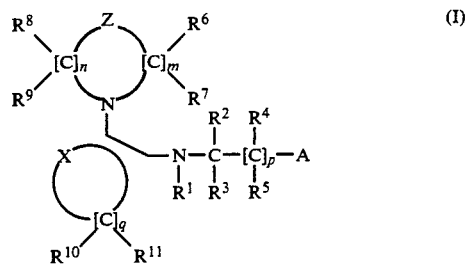

wherein $R^1$ is selected from hydrido, alkyl, cycloalkyl, hydroxyalkyl, haloalkyl, cycloalkylalkyl, alkoxyalkyl, aralkyl, aryl, alkenylalkyl, alkynylalkyl, carboxyalkyl, alkanoyl, alkylsulfinyl, alkylsulfonyl, arylsulfinyl and arylsulfonyl; wherein each of $R^2$ and $R^3$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy, cyanoalkyl, alkylsulfinyl, alkylsulfonyl, arylsulfinyl and arylsulfonyl; wherein $R^2$ and $R^3$ may be taken together to form a saturated or partially unsaturated carbocyclic group having three to eight ring carbons; wherein each of $R^4$ through $R^{11}$ is independently selected from hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl and alkynyl; wherein $R^4$ and $R^5$ may be taken together to form oxo or to form a saturated or partially unsaturated carbocyclic group having three to eight ring carbons; wherein $R^6$ and $R^7$ may be taken together to form oxo; wherein $R^8$ and $R^9$ may be taken together to form oxo; wherein $R^{10}$ and $R^{11}$ may be taken together to form oxo; wherein each of n and m is a number selected from one through four; wherein each of p and q is a number selected from zero through five; wherein each of X and Z is independently selected from

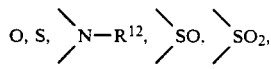

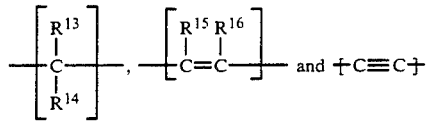

wherein $R^{12}$ may be selected from hydrido, alkyl, cycloalkyl, cycloalkylalkyl, aryl, aralkyl, heteroaryl, alkoxyalkyl, hydroxyalkyl, alkanoyl, aralkanoyl, aroyl, aminoalkyl, monoalkylaminoalkyl and dialkylaminoalkyl; wherein each of $R^{13}$ through $R^{16}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically-acceptable salt thereof.

The family of compounds within Formula I is novel with the proviso that each of the compounds embraced by Formula I is a cis isomer with respect to the two nitrogen atoms of Formula I; or a pharmaceutically acceptable salt thereof.

A preferred family of compounds of Formula I consists of those compounds wherein $R^1$ is selected from hydrido, alkyl, cycloalkyl, hydroxyalkyl, haloalkyl, cycloalkylalkyl, alkoxyalkyl, aralkyl, aryl, alkenylalkyl, alkynylalkyl and carboxyalkyl; wherein each of $R^2$ and $R^3$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy and cyanoalkyl; wherein $R^2$ and $R^3$ may be taken together to form a saturated or partially unsaturated carbocyclic group having three to eight ring carbons; wherein each of $R^4$ through $R^{11}$ is independently selected from hydrido, hydroxy, alkyl, cycloalkyl, cycloalkylalkyl, aralkyl, aryl, alkoxy, aryloxy, aralkoxy, alkoxyalkyl, haloalkyl, hydroxyalkyl, cyano, amino, monoalkylamino, dialkylamino, carboxy, carboxyalkyl, alkanoyl, alkenyl and alkynyl; wherein $R^4$ and $R^5$ may be taken together to form oxo or to form a saturated or partially unsaturated carbocyclic group having three to eight ring carbons; wherein each of n and m is a number selected from one through four; wherein each of p and q is a number selected from zero through five; wherein X is selected from

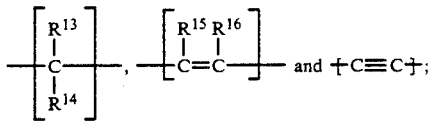

wherein Z is selected from

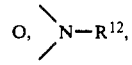

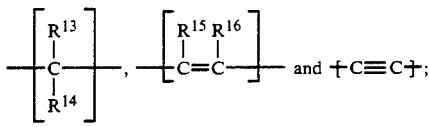

wherein $R^{12}$ may be selected from hydrido, alkyl, cycloalkyl, cycloalkylalkyl, aryl, aralkyl, heteroaryl, alkoxyalkyl, hydroxyalkyl, alkanoyl, aralkanoyl, aroyl, aminoalkyl, monoalkylaminoalkyl and dialkylaminoalkyl; wherein each of $R^{13}$ through $R^{16}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl and alkanoyl; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically acceptable salt thereof.

A more preferred family of compounds within Formula I consists of those compounds wherein $R^1$ is selected from hydrido, loweralkyl, cycloalkyl of three to about eight carbon atoms, hydroxyloweralkyl, haloloweralkyl, cycloalkylalkyl of four to about eight carbon atoms, loweralkoxyloweralkyl, phenylloweralkyl, phenyl, loweralkenylloweralkyl, loweralkynylloweralkyl and carboxyloweralkyl; wherein each of $R^2$ and $R^3$ is independently selected from hydrido, loweralkyl, cycloalkyl of three to about eight carbon atoms, hydroxyloweralkyl, haloloweralkyl, cycloalkylalkyl of four to about eight carbon atoms, loweralkoxyloweralkyl, phenylloweralkyl, phenyl, loweralkenyl, loweralkynyl, loweralkenylloweralkyl, loweralkynylloweralkyl, carboxyloweralkyl, loweralkanoyl, loweralkoxycarbonyl, carboxy and cyanoloweralkyl; wherein $R^2$ and $R^3$ may be taken together to form a saturated or partially unsaturated carbocyclic group having three to eight ring carbons; wherein each of $R^4$ through $R^{11}$ is independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenylloweralkoxy, loweralkoxyloweralkyl, haloloweralkyl, hydroxyloweralkyl, cyano, amino, monoloweralkylamino, diloweralkylamino, carboxy, carboxyloweralkyl, loweralkanoyl, loweralkenyl and loweralkynyl; wherein $R^4$ saturated or partially unsaturated carbocyclic group having three to eight ring carbons; wherein each of n and m is a number selected from one through four; wherein each of p and q is a number selected from zero through five; wherein X is selected from

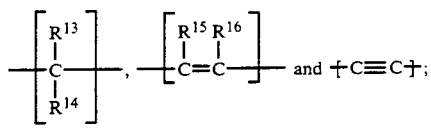

wherein Z is selected from

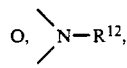

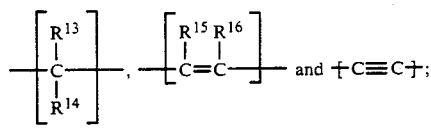

wherein $R^{12}$ may be selected from hydrido, loweralkyl, cycloalkyl of three to about eight carbon atoms, cycloalkylalkyl of four to about eight carbon atoms, phenyl, phenylloweralkyl, heteroaryl, loweralkoxyloweralkyl, hydroxyloweralkyl, loweralkanoyl, phenylalkanoyl, benzoyl, aminoloweralkyl, monoloweralkylaminoloweralkyl and diloweralkylaminoloweralkyl; wherein each of $R^{13}$ through $R^{16}$ is independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenylloweralkoxy, phenoxy, loweralkoxyloweralkyl, haloloweralkyl, hydroxyloweralkyl, halo, cyano, amino, monoloweralkylamino, diloweralkylamino, carboxy, carboxyloweralkyl and loweralkanoyl; wherein A is selected from phenyl, naphthyl, heteroaryl, phenoxy, naphthyloxy, heteroaryloxy, phenylloweralkoxy, naphthylloweralkoxy, heteroarylloweralkoxy, phenylamino, naphthylamino, heteroarylamino, phenylloweralkylamino, naphthylloweralkylamino, heteroaralkylamino, phenylthio, naphthylthio, heteroarylthio, phenylloweralkylthio and heteroarylloweralkylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenyloweralkoxy, loweralkoxyloweralkyl, halo, haloloweralkyl, hydroxyloweralkyl, cyano, amino, monoloweralkylamino, diloweralkylamino, carboxy, carboxyloweralkyl, loweralkanoyl, loweralkenyl and loweralkynyl; or a pharmaceutically acceptable salt thereof.

A more highly preferred family of compounds of Formula I consists of those compounds wherein $R^1$ is selected from hydrido, loweralkyl, cycloalkyl of three to about eight carbon atoms, cycloalkylalkyl of four to about eight carbon atoms, benzyl, phenyl, loweralkenylloweralkyl and loweralkynylloweralkyl; wherein each of $R^2$ and $R^3$ is independently selected from hydrido, loweralkyl, cycloalkyl of three to about eight carbon atoms, cycloalkylalkyl of four to about eight carbon atoms, benzyl, phenyl, loweralkenyl, loweralkynyl, loweralkenylloweralkyl, loweralkynylloweralkyl, loweralkanoyl and loweralkoxycarbonyl; wherein $R^2$ and $R^3$ may be taken together to form a saturated or partially unsaturated carbocyclic group having three to eight ring carbons; wherein each of $R^4$ through $R^{11}$ is independently selected from hydrido, hydroxy, loweralkyl, cycloalkyl of three to about eight carbon atoms, cycloalkylalkyl of four to about eight carbon atoms, benzyl, phenyl, loweralkoxy, phenoxy, benzyloxy, loweralkoxyloweralkyl, haloloweralkyl, hydroxyloweralkyl, loweralkanoyl, loweralkenyl and loweralkynyl; wherein $R^4$ and $R^5$ may be taken together to form oxo or to form a saturated or partially unsaturated carbocyclic group having three to eight ring carbons; wherein each of n and m is a number selected from one through four; wherein each of p and q is a number selected from zero through five; wherein X is selected from

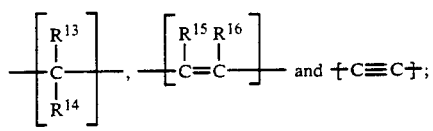

wherein Z is selected from

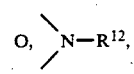

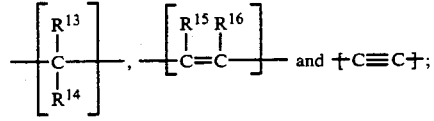

wherein $R^{12}$ may be selected from hydrido, loweralkyl, cycloalkyl of three to about eight carbon atoms, cycloalkylalkyl of four to about eight carbon atoms, phenyl, benzyl, loweralkoxyloweralkyl and hydroxyloweralkyl; wherein each of $R^{13}$ through $R^{16}$ is independently selected from hydrido, hydroxy, loweralkyl, cycloalkyl of three to about eight carbon atoms, cycloalkylalkyl of four to about eight carbon atoms, benzyl, phenyl, loweralkoxy, benzyloxy, phenoxy, loweralkoxyloweralkyl, haloloweralkyl, hydroxyloweralkyl and halo; wherein A is selected from phenyl, naphthyl, thienyl, phenoxy, benzyloxy, naphthyloxy, thiophenoxy, phenylamino, benzylamino, naphthylamino, phenylthio, benzylthio and naphthylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, loweralkoxy, loweralkoxyloweralkyl, halo, haloloweralkyl, hydroxyloweralkyl, amino, monoloweralkylamino, diloweralkylamino, loweralkanoyl, loweralkenyl and loweralkynyl; or a pharmaceutically acceptable salt thereof.

A family of compounds of particular interest within Formula I are compounds embraced by Formula II:

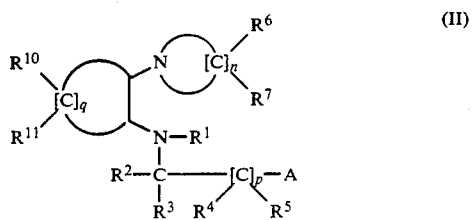

wherein $R^1$ is selected from hydrido, loweralkyl, cycloalkylalkyl of four to six carbon atoms and loweralkenylloweralkyl; wherein each of $R^2$ and $R^3$ is independently selected from hydrido and loweralkyl; wherein each of $R^4$ through $R^7$, $R^{10}$ and $R^{11}$ is independently selected from hydrido, hydroxy, loweralkyl, benzyl, phenoxy, benzyloxy and haloloweralkyl; wherein n is a number selected from four through six; wherein p is a number selected from zero through four; wherein q is a number selected from three through five; wherein A is selected from phenyl, naphthyl and thienyl; wherein any of the foregoing A groups can be further substituted with one or more substituents independently selected from hydrido, hydroxy, loweralkyl, loweralkoxy, halo, haloloweralkyl, amino, monoloweralkylamino and diloweralkylamino; or a pharmaceutically acceptable salt thereof.

A more preferred family of compounds within Formula II consists of compounds wherein $R^1$ is selected from hydrido, methyl, ethyl, propyl, cyclopropylmethyl, allyl and dimethylallyl; wherein each of $R^2$ and $R^3$ is independently selected from hydrido, methyl, ethyl and propyl; wherein each of $R^4$ through $R^7$, $R^{10}$ and $R^{11}$ is independently selected from hydrido, hydroxy, methyl, ethyl, propyl, benzyl, phenoxy, benzyloxy and haloloweralkyl; wherein n is a number selected from four or five; wherein p is a number selected from zero through two; wherein q is a number selected from three or four; wherein A is phenyl or naphthyl; wherein any of the foregoing A groups can be further substituted with one or more substituents independently selected from hydroxy, methyl, ethyl, propyl, methoxy, ethoxy, methylenedioxy, halo, trifluoromethyl, amino, methylamino and dimethylamino; or a pharmaceutically acceptable salt thereof.

Of highest interest are the following specific compounds:

(±)-cis-N-[2-(3,4-dichlorophenyl)ethyl]-2-(1-pyrrolidinyl)-cyclohexylamine;
1S, 2R-(+)-cis-N-[2-(3,4-dichlorophenyl)ethyl]-2-(1-pyrrolidinyl)cyclohexylamine;
1R, 2S-(−)-cis-N-[2-(3,4-dichlorophenyl)ethyl]-2-(1-pyrrolidinyl)cyclohexylamine;
(±)-cis-N-[2-(3,4-dichlorophenyl)ethyl]-N-methyl-2-(1-pyrrolidinyl)cyclohexylamine;
1S, 2R-(−)-cis-N-[2-(3,4-dichlorophenyl)ethyl]-N-methyl-2-(1-pyrrolidinyl)cyclohexylamine;
1R, 2S-(+)-cis-N-[2-(3,4-dichlorophenyl)ethyl]-N-methyl-2-(1-pyrrolidinyl)cyclohexylamine;
(±)-cis-N-methyl-N-(2-phenylethyl)-2-(1-pyrrolidinyl)-cyclohexylamine;
(+)-cis-N-methyl-N-[2-(β-naphthyl)ethyl]-2-(1-pyrrolidinyl)-cyclohexylamine;
1S, 2R-(−)-cis-N-methyl-N-[2-(3,4-methylenedioxyphenyl)-ethyl]-2-(1-pyrrolidinyl)cyclohexylamine;
1R, 2S-(+)-cis-N-methyl-N-[2-(3,4-methylenedioxyphenyl)-ethyl]-2-(1-pyrrolidinyl)cyclohexylamine;
1R, 2S-(−)-cis-N-[2-(3,4-dichlorophenyl)ethyl]-N-ethyl-2-(1-pyrrolidinyl)cyclohexylamine;
1R, 2S-(−)-cis-N-cyclopropylmethyl-N-[2-(3,4-dichlorophenyl)ethyl]-2-(1-pyrrolidinyl)cyclohexylamine; and
1R, 2S-(−)-cis-N-[2-(3,4-dichlorophenyl)ethyl]-N-(1-propyl)-2-(1-pyrrolidinyl) cyclohexylamine.

The term "hydrido" denotes a single hydrogen atom (H) which may be attached, for example, to an oxygen atom to form hydroxyl group. Where the term "alkyl" is used, either alone or within other terms such as "haloalkyl" and "hydroxyalkyl", the term "alkyl" embraces linear or branched radicals having one to about twenty carbon atoms or, preferably, one to about ten carbon atoms. More preferred alkyl radicals are "lower alkyl" radicals having one to about five carbon atoms. The term "cycloalkyl" embraces cyclic radicals having three to about six carbon atoms, such as cyclopropyl and cyclobutyl. The term "haloalkyl" embraces radicals wherein any one or more of the alkyl carbon atoms is substituted with one or more halo groups, preferable selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. An example of a polyhaloalkyl is a trifluoromethyl group. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferable two to about ten carbon atoms, and containing at least one carbon-carbon triple bond. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. The term "alkylene chain" describes a chain of two to six methylene (—$CH_2$—) groups which may form a cyclic structure with or without a hetero atom in the cyclic structure.

Specific examples of alkyl groups are methyl, ethyl, n-propyl, isopropyl, n-butyl, sec-butyl, iso-butyl, tertbutyl, n-pentyl, iso-pentyl, methyl-butyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Included within the family of compounds of Formulas I-II are the tautomeric forms of the described compounds, isomeric forms including diastereoisomers, and the pharmaceutically-acceptable salts thereof. The term "pharmaceutically-acceptable salts" embraces salts commonly used to form alkali metal salts and to form addition salts of free acids or free bases. Since the compounds of Formulas I-II contain basic nitrogen atoms, such salts are typically acid addition salts. The phrase "pharmaceutically-acceptable salts" is not intended to embrace quaternary ammonium salts. The nature of the salt is not critical, provided that it is pharmaceutically acceptable, and acids which may be employed to form salts are, of course, well known to those skilled in this art. Examples of acids which may be employed to form pharmaceutically acceptable acid addition salts include such inorganic acids as hydrochloric acid, sulfuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of Formulas I-II General Synthetic Procedures Compounds of Formulas I and II may be prepared in accordance with the following generic procedures, within which specific schemes are shown for Formula II type compounds.

Step 1

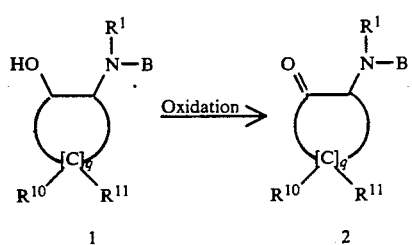

wherein $R^1$, $R^{10}$, $R^{11}$, and q are as defined previously; and wherein B represents a protecting group such as acetyl, benzoyl, t-butyloxy-carbonyl or benzyloxycarbonyl.

A process for preparing the compounds of the invention starts with protected hydroxyamines of general structure 1 where $R^1$, $R^{10}$, $R^{11}$, and q have the value assigned previously; and where B represents a protecting group such as acetyl, benzoyl or t.-butyloxycarbonyl. The alcohol is oxidized to the ketone 2 employing oxidizing agents such as pyridinium chlorochromate, chromium trioxide, potassium dichromate, or other oxidizing agents familiar to those skilled in the art. This oxidation can be achieved in either aqueous or organic solvents, depending on the oxidizing agent of choice, and at temperatures ranging from $-60°$ to reflux of the reaction mixture.

Step 2

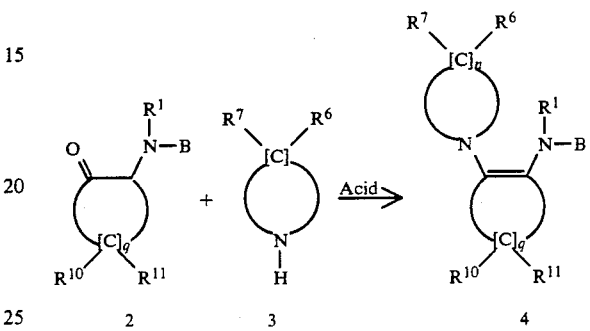

wherein B, $R^1$, $R^6$, $R^7$, $R^{10}$, $R^{11}$, n, and q are as defined previously.

In the second step of the process, ketones of general structure 2 are converted to enamines of general structure 4 by mixing 2 with amines of general structure 3 where B, $R^1$, $R^6$, $R^7$, $R^{10}$, $R^{11}$, n, and q are as defined previously. The compounds can be combined neat or in a variety of solvents such as toluene, xylene, or chloroform and with an acid such as p-toluenesulfonic acid, acetic acid, or trifluoroacetic acid. The temperature of the reaction can vary from room temperature to reflux of the reaction mixture.

Step 3

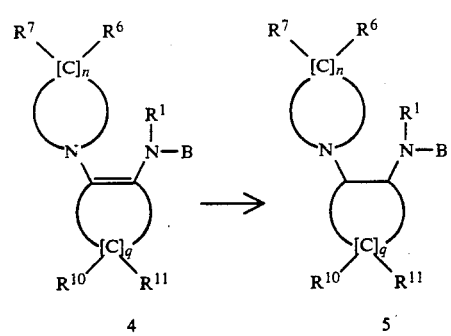

wherein B, $R^1$, $R^6$, $R^7$, $R^{10}$, $R^{11}$, n, and q are as defined previously.

In the third step of the process, enamines of general structure 4 are reduced to amines of general structure 5 by employing reducing agents such as lithium aluminum hydride, sodium borohydride, sodium cyanoborohydride, catalytic hydrogenation, or other reducing agents familiar to those skilled in the art. This reduction can be accomplished in either protic or aprotic solvents, depending on the reducing agent of choice, and at temperatures ranging from room temperature to reflux of the reaction mixture.

Step 4(a)

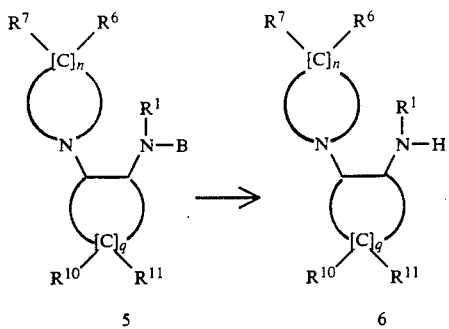

wherein B, $R^1$, $R^6$, $R^7$, $R^{10}$, $R^{11}$, n, and q are as defined previously.

In the fourth step of the process, amines of general structure 5 are converted to amines of general structure 6 by removal of the blocking group B. The conversion is best achieved by mixing 5 with a base such as sodium hydroxide, potassium hydroxide or other bases familiar to those skilled in the art. The reagents are combined in a protic solvent such as water, ethylene glycol, or methanol. The temperature of the reaction can vary from room temperature to reflux of the reaction mixture.

Step 4(b)

Alternately, amines of general structure 6 can be prepared from amines of general structure 5 by removal of the blocking group B by mixing 5 with an acid such as hydrochloric acid, sulfuric acid, trifluoroacetic acid or other acids familiar to those skilled in the art. The reagents are combined in a protic solvent such as water, ethylene glycol, or methanol. The temperature of the reaction can vary from room temperature to reflux of the reaction mixture.

Step 5(a)

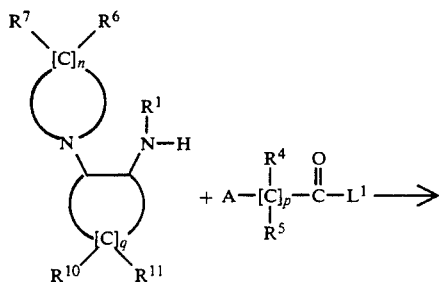

-continued
Step 5(a)

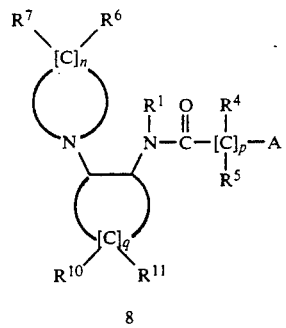

wherein A, $R^1$, $R^4$ through $R^7$, $R^{10}$, $R^{11}$, n, p, and q are as defined previously; and wherein $L^1$ is a good leaving group such as chloro, bromo, acyloxy, or hydroxy.

In the fifth step of the process, amines of general structure 6 are converted to amides of general structure 8 where A, $R^4$, and $R^5$ have the value assigned previously and $L^1$ is a good leaving group such as chloro, bromo, acyloxy, or hydroxy. The conversion can be best achieved by mixing the reagents neat or in an aprotic solvent such as tetrahydrofuran, methylene chloride, or ether. The reaction can be run in the absence or presence of an activating agent such as dicyclohexylcarbodiimide or phosphorus oxychloride, depending on the leaving group of choice. The temperature of the reaction can vary from 0° to reflux of the reaction mixture.

Step 6(a)

wherein A, $R^1$, $R^4$ through $R^7$, $R^{10}$, $R^{11}$, n, p, and q are as defined previously.

In the sixth step of the process, amides of general structure 8 are converted to amines of general structure 9 by employing reducing agents such as lithium aluminum hydride, sodium borohydride, sodium cyanoborohydride, or other reducing agents familiar to those skilled in the art. This reduction can be accomplished in either protic or aprotic solvents, depending on the reducing agent of choice, and at temperatures ranging from room temperature to reflux of the reaction mixture.

Step 5(b)

Alternately, amines of general structure 11 can be prepared according to the following generic procedure.

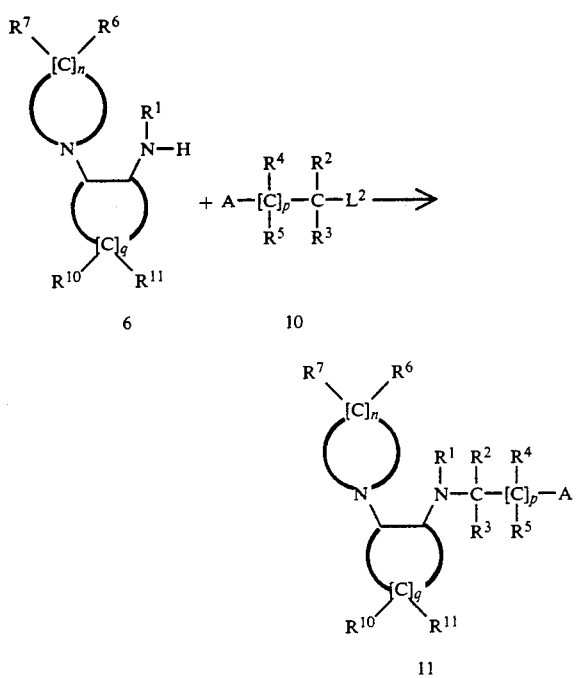

wherein A, $R^1$ through $R^7$, $R^{10}$, $R^{11}$, n, p, and q are as defined previously; and wherein $L^2$ is a good leaving group such as halogen, tosylate, mesylate, brosylate or OH.

Amines of general structure 11 can be alternately prepared by combining amines of general structure 6 with compounds of general structure 10 where A, $R^1$ through $R^7$, $R^{10}$, $R^{11}$, n, p, and q have the values assigned previously and where $L^2$ is a good leaving group such as halogen, tosylate, mesylate, brosylate or OH. The compounds can be combined in a variety of solvents such as toluene, xylenes, dimethylformamide, hexamethylphosphoramide, or ethanol. The temperature of the reaction can vary from room temperature to reflux of the reaction mixture.

The following Examples I≅XI are detailed descriptions of the methods of preparation of compounds of Formula I. These detailed preparations fall within the scope of, and serve to exemplify, the above described Generic Procedures which form part of the invention. These Examples I-XI are presented for illustrative purposes only and are not intended as a restriction on the scope of the invention. All parts are by weight unless otherwise indicated. Most of the commercially available starting materials were obtained from Aldrich Chemical Company, Milwaukee, Wis.

EXAMPLE I (±)-trans-2-Benzamidocyclohexanol (±)-trans-2-Aminocyclohexanol (241 gm) was combined with chloroform (2000 ml), water (2000 ml) and sodium bicarbonate (352 gm) and stirred. Benzoyl chloride (352 gm) was added dropwise to the stirred solution and stirring was continued for 1 hr. The product was filtered and washed with water. The white solid was dried at 80° C. to provide the product (mp 172°-173° C.).

EXAMPLE II (±)-2-Benzamidocyclohexanone

A solution of Jones reagent (1135 ml) was prepared by combining $CrO_3$ (140 gm) and $H_2SO_4$ (122 ml) with water. The Jones reagent was added dropwise to a cooled, stirred mixture of (±)-trans-2-benzamidocyclohexanol (260 gm) and acetone (3000 ml) and the stirring continued 1 hr. A 20% solution of $K_2CO_3$ in water was added to the reaction solution until the evolution of carbon dioxide subsided. The resulting layers were separated and the bottom layer extracted with ethyl acetate. The ethyl acetate was combined with the material from the upper layer and the resulting solution washed with water and saturated sodium chloride solution. The organic solution was concentrated on a rotary evaporator and the residue was recrystallized from aqueous 2-propanol to provide the product (mp 126°-127° C.).

EXAMPLE III (±)-cis-2-(1-Pyrrolidinyl)-N-benzoylcyclohexylamine hydrochloride (±)-2-Benzamidocyclohexanone (213 gm) was combined with pyrrolidine (103 ml), p-toluenesulfonic acid (9.3 gm) and benzene (3300 ml) and heated to reflux for 23 hours. Additional pyrrolidine (103 ml) was added to the reaction mixture and the heating continued for 24 hours. The solvent was removed on a rotary evaporator to provide a crude enamine mixture. The crude material was dissolved in ethyl acetate (100 gm/200 ml) and hydrogenated over 10% Pd on carbon at 50 psi for 1.5 hours. The mixture was filtered through celite and the filtrate was concentrated on a rotary evaporator. The residue was combined with citric acid monohydrate (306 gm), water (1300 ml) and methylene chloride (500 ml) and shaken until all solid material had dissolved. The layers were separated and the aqueous layer was washed with additional methylene chloride. Excess concentrated aqueous ammonia was added to the aqueous solution and the mixture extracted with methylene chloride. The combined organic extracts were dried ($Na_2SO_4$) and the solvent removed on a rotary evaporator. The crude material was dissolved in methanol (200 ml) and treated with an excess of a solution of anhydrous hydrogen chloride in methanol. The solution was adjusted to a final volume of 700 ml by the addition of 2-propanol and the methanol was removed by distillation while maintaining a constant volume of 700 ml by the slow addition of 2-propanol. The crude product crystallized upon slow cooling and was filtered. The material was recrystallized from 2-propanol to provide the product (mp 276°-277° C.).

EXAMPLE IV (±)-cis-2-(1-Pyrrolidinyl)cyclohexylamine (±)-cis-2-(1-Pyrrolidinyl)-N-benzoylcyclohexylamine hydrochloride (10 gm) was combined with ethylene glycol (50 ml) and potassium hydroxide (10 gm) and the solution was heated to reflux for 48 hours. The solution was diluted with water (200 ml) and extracted with ether. The ether was removed on a rotary evaporator and the residue was distilled (94° C. at 0.05 mm Hg) to provide the product.

EXAMPLE V (−)-cis-2-(1-Pyrrolidinyl)cyclohexylamine (±)-cis-2-(1-pyrrolidinyl)cyclohexylamine (10 gm) was combined with ethanol (10 ml) and 2-propanol (40 ml) and warmed to 60° C. A solution of R-(−)-mandelic acid (18 gm) in ethanol (50 ml) and 2-propanol (200 ml) was warmed to 60° C. and added to the amine solution. The solution was allowed to cool slowly to room temperature and the resulting crystals were filtered. The crystals were washed with 20% ethanol in 2-propanol, followed by ether and dried under vacuum. The crystals were recrystallized from 20% ethanol in 2-propanol to provide the mandelate salt. The salt was partitioned between 30% NaOH and chloroform and the layers separated. The chloroform was removed on a rotary evaporator to provide the product as a colorless oil which solidified upon standing (bp 86° C., at 0.1 mm Hg, $[\alpha]_D(\text{MeOH}) = -2.95°$).

EXAMPLE VI (+)-cis-2-(1-Pyrrolidinyl)cyclohexylamine

The mother liquors from Example V were concentrated on a rotary evaporator. The residue was partitioned between 30% NaOH and chloroform and the layers separated. The chloroform was removed on a rotary evaporator and the residue was distilled under high vacuum. The distillate was combined with ethanol (10 ml) and 2-propanol (40 ml) and warmed to 60° C. A solution of R-(−)-mandelic acid (18 gm) in ethanol (50 ml) and 2-propanol (200 ml) was warmed to 60° C. and added to the amine solution. The solution was allowed to cool slowly to room temperature and the resulting crystals were filtered. The crystals were washed with 20% ethanol in 2-propanol, followed by ether and dried under vacuum. The crystals were recrystallized from 20% ethanol in 2-propanol to provide the mandelate salt. The salt was partitioned between 30% NaOH and chloroform and the layers separated. The chloroform was removed on a rotary evaporator to provide the product as a colorless oil which solidified upon standing (bp 86° C. at 0.1 mm Hg, $[\alpha]_D(\text{MeOH}) = -+2.21\sqrt{\ })$.

EXAMPLE VII 1R,2S-(−)-cis-2-(1-Pyrrolidinyl)-N-methylcyclohexylamine (−)-cis-2-(1-pyrrolidinyl)cyclohexylamine (2 gm) was combined with ethyl formate (20 ml) and heated to reflux 10 minutes. The solvent was removed on a rotary evaporator. The residue was combined with anhydrous tetrahydrofuran (10 ml) and treated with 1 M lithium aluminum hydride in tetrahydrofuran (16 ml). The mixture was heated to reflux 1 hour and cooled in an ice bath. The mixture was treated with water (2.4 ml) and 15% NaOH (0.6 ml), filtered, and the solvent removed on a rotary evaporator. The residue was distilled under high vacuum to provide the product as a colorless oil (bp 76° C. at 1.1 mm Hg, $[\alpha]_D(\text{MeOH}) = -31.7°$).

EXAMPLE VIII (±)-2-(N-t-Butyloxycarbonyl-N-methylamino)cyclohexanone (±)-trans-N-methyl-2-aminocyclohexanol (142 gm) was combined with t-butyldicarbonate (240 gm), potassium bicarbonate (458 gm), and water (1000 ml) and stirred overnight. The aqueous mixture was extracted with methylene chloride and the organic extract was dried (Na$_2$SO$_4$) and concentrated on a rotary evaporator. The residue was recrystallized from isooctane to provide a white solid (mp 82°-83° C.). The solid was dissolved in methylene chloride (500 ml) and added dropwise to a stirred solution of pyridinium chlorochromate (334 gm) in methylene chloride (1000 ml). After the addition, stirring was continued for 3 hours. The mixture was diluted with ether (1500 ml) and filtered through florisil. The solvent was removed on a rotary evaporator and the residue was distilled (115° C. at 0.9 mm Hg) to provide a colorless oil.

EXAMPLE IX (±)-cis-2-[1-Pyrrolidinyl]-N-methylcyclohexylamine (±)-cis-2-Pyrrolidinyl-N-t-butyloxycarbonyl-N-methylcyclohexylamine (247 gm) was slowly added to 6 M hydrochloric acid at 60° C. with vigorous stirring. The solution was stirred an additional 5 minutes at 60° C. and poured onto ice (200 gm). Excess concentrated aqueous ammonia was added and the mixture was extracted with methylene chloride. The combined extracts were dried (Na$_2$SO$_4$) and the solvent removed on a rotary evaporator. The residue was distilled (78° C. at 0.3 mm Hg) to give the product as a colorless oil.

EXAMPLE X (±)-cis-N-[2-(3,4-Dichlorophenyl)ethyl]-N-methyl-2-(1-pyrrolidinyl)cyclohexylamine (Compound No. 1).

(±)-cis-2-Pyrrolidinyl-N-methylcyclohexylamine (3 gm) was combined with anhydrous dimethylformamide (70 ml) and warmed to 60° C. 2-(3,4-dichlorophenyl)ethyl methanesulfonate (14 gm) was added to the warm amine solution over 3 days. The reaction mixture was diluted to 500 ml with water and extracted with chloroform. The combined extracts were washed with water and treated with a solution of hydrogen bromide in methanol. The solution was concentrated on a rotary evaporator and the residual dimethylformamide removed by distillation under high vacuum. The residue was triturated with 2-propanol to provide a white solid. The solid was recrystallized from 2-propanol. Analytical data are reported in Table I.

EXAMPLE IX (±)-cis-N-[2-(3,4-dichlorophenyl)ethyl]-2-(1-pyrrolidinyl)-cyclohexylamine (Compound No. 8)

(±)-cis-2-(1-pyrrolidinyl)cyclohexylamine (5 gm) was combined with pyridine (1.2 gm), chloroform (200 ml), 3,4-dichlorophenylacetic acid (9.15 gm), and dicyclohexylcarbodiimide (12.3 gm) and the mixture was stirred for 12 hr at room temperature. The mixture was filtered, the precipitate was washed with ether (100 ml) and the filtrate and ether wash were combined. The organic solution was diluted with ether (200 ml) and extracted with 10% citric acid in water (300 ml). The acid layer was washed with ether (2×200 ml), then treated with excess concentrated aqueous ammonia until basic. The resulting mixture was extracted with methylene chloride (2×200 ml) and the combined organic extracts were washed with water (2×50 ml) and concentrated on a rotary evaporator. The resulting white solid was combined with tetrahydrofuran (25 ml) and added dropwise to a solution of $AlH_3$ in tetrahydrofuran (76.2 ml of a 0.665 M solution) at room temperature. After the addition, the mixture was poured into 15% NaOH and the resulting mixture was extracted with ether (3×100 ml). The ether was removed on a rotary evaporator and the residue was dissolved in ethanol (100 ml). The ethanol was removed on a rotary evaporator and the residue was converted to the hydrogen bromide salt which was recrystallized from ethanol. Analytical data are reported in Table I.

Table I is a list of 13 specific compounds of most interest within Formula I. The preparation of representative compounds from Table I is described in detail in Example Procedures I-XI, above. The remaining compounds may likewise be prepared in accordance with the above-described Example Procedures.

TABLE I

| Compound No. | Name | Structure | Elemental Analysis Theor. | Elemental Analysis Found | Melting Point | Specific Rotation [α]$_D$ | Mass Spectral Analysis |
|---|---|---|---|---|---|---|---|
| 1 | (±)-cis-N-[2-(3,4-dichlorophenyl)ethyl]-N-methyl-2-(1-pyrrolidinyl)cyclohexylamine.oxalate | 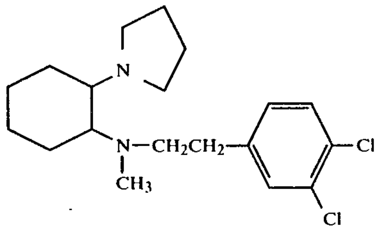 | C 56.63<br>H 6.79<br>N 6.29 | 56.43<br>6.91<br>6.33 | 120–125° C. | — | — |
| 2 | S,2R-(−)-cis-N-[2-(3,4-dichlorophenyl)ethyl]-N-methyl-2-(1-pyrrolidinyl)cyclohexylamine.2HBr | 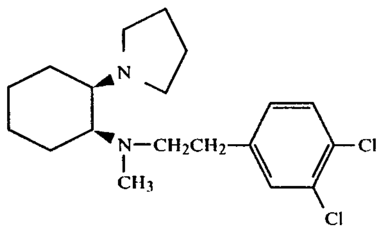 | C 44.12<br>H 5.85<br>N 5.42 | 44.07<br>5.88<br>5.44 | 215–217° C. | −8.6° C.<br>(0.84, MeOH) | |
| 3 | 1R,2S-(+)-cis-N-[2-(3,4-dichlorophenyl)ethyl]-N-methyl-2-(1-pyrrolidinyl)cyclohexylamine.2HBr | 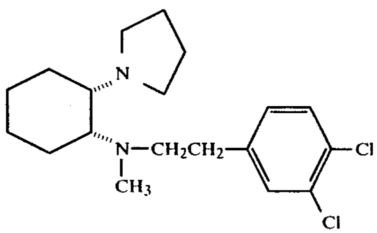 | C 44.12<br>H 5.85<br>N 5.42 | 44.21<br>5.91<br>5.40 | 217–218° C. | +8.0° C.<br>(0.57, MeOH) | |
| 4 | (±)-cis-N-methyl-N-(2-phenylethyl)-2-(1-pyrrolidinyl)cyclohexylamine | 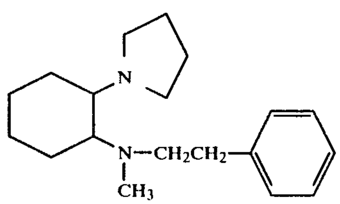 | — | — | oil | | M$^+$ (found) 286.242<br>Requires 286.241 |

TABLE I-continued

| Compound No. | Name | Structure | Elemental Analysis Theor. | Elemental Analysis Found | Melting Point | Specific Rotation [α]D | Mass Spectral Analysis |
|---|---|---|---|---|---|---|---|
| 5 | (±)-cis-N-methyl-N-[2-(2-naphthyl)ethyl]-2-(1-pyrrolidinyl)cyclohexylamine | 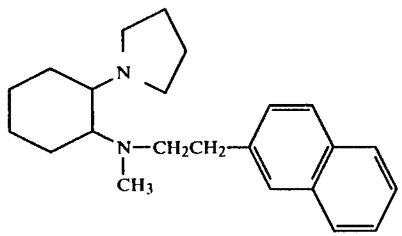 | — | — | oil | — | M+ (found) 336.256 Requires 335.257 |
| 6 | 1S,2R-(−)-cis-N-methyl-N-[2-(3,4-methylenedioxyphenyl)ethyl]-2-(1-pyrrolidinyl)cyclohexylamine.2HBr | 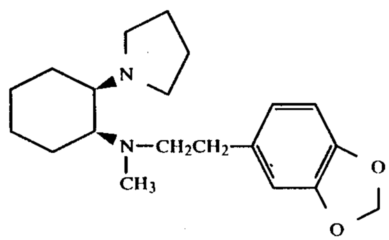 | C 48.79<br>H 6.55<br>N 5.69 | 48.68<br>6.59<br>5.68 | 248–249° C. | −13.0° C.<br>(3.99, H₂O) | — |
| 7 | 1R,2S-(+)-cis-N-methyl-N-[2-(3,4-methylenedioxyphenyl)ethyl]-2-(1-pyrrolidinyl)cyclohexylamine.2HBr | 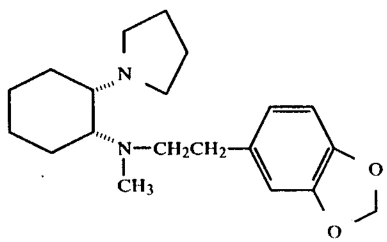 | C 48.79<br>H 6.55<br>N 5.69 | 48.64<br>6.60<br>5.62 | 248–249° C. | +15.2° C.<br>(2.16, H₂O) | — |
| 8 | (±)-cis-N-[2-(3,4-dichlorophenyl)ethyl]-2-(1-pyrrolidinyl)-cyclohexylamine.2HBr | 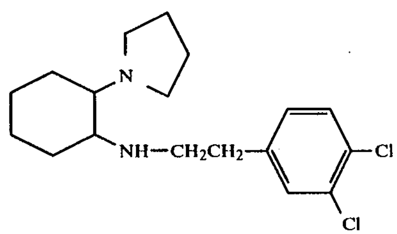 | C 42.96<br>H 5.57<br>N 5.57 | 43.04<br>5.65<br>5.54 | 274–275° C. | — | — |

TABLE I-continued

| Compound No. | Name | Structure | Elemental Analysis Theor. | Found | Melting Point | Specific Rotation [α]D | Mass Spectral Analysis |
|---|---|---|---|---|---|---|---|
| 9 | 1S,2R-(+)-cis-N-[2-(3,4-dichlorophenyl)ethyl]-2-(1-pyrrolidinyl)cyclohexylamine.2HBr | 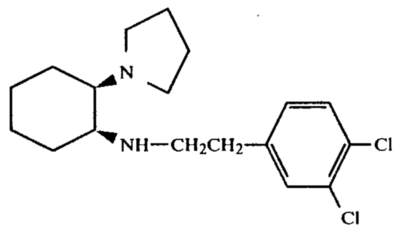 | C 42.96<br>H 5.57<br>N 5.57 | 43.03<br>5.62<br>5.59 | 280.5–281.5° C. | +11.5° C.<br>(0.57, MeOH) | |
| 10 | 1R,2S-(−)-cis-N-[2-(3,4-dichlorophenyl)ethyl]-2-(1-pyrrolidinyl)cyclohexylamine.2HBr | 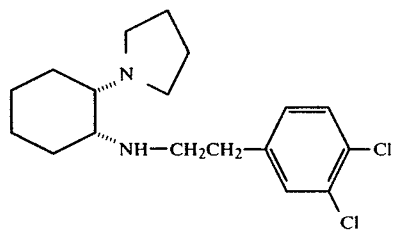 | C 42.96<br>H 5.57<br>N 5.57 | 43.03<br>5.61<br>5.57 | 280–281° C. | −11.1° C.<br>(0.32, MeOH) | — |
| 11 | 1R,2S-(−)-cis-N-[2-(3,4-dichlorophenyl)ethyl]-N-ethyl-2-(1-pyrrolidinyl)cyclohexylamine.2HI | 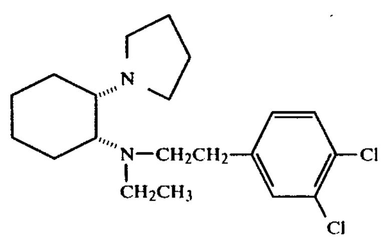 | C 38.40<br>H 5.12<br>N 4.48 | 38.47<br>5.22<br>4.51 | 225.5–226° C. | −2.1° C.<br>(0.42, MeOH) | |
| 12 | 1R,2S-1-)-cis-N-[2-(3,4-dichlorophenyl)ethyl]-N-cyclopropylmethyl-2-(1-pyrrolidinyl)cyclohexylamine.2fumarate | 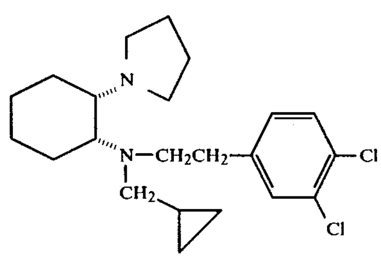 | C 57.42<br>H 6.38<br>N 4.47 | 57.41<br>6.57<br>4.72 | 152–154° C. | −23.8° C.<br>(.039, MeOH) | |

TABLE I-continued

| Compound No. | Name | Structure | Elemental Analysis Theor. | Elemental Analysis Found | Melting Point | Specific Rotation [α]$_D$ | Mass Spectral Analysis |
|---|---|---|---|---|---|---|---|
| 13 | 1R,2S-(−)-cis-N-[2-(3,4-dichlorophenyl)ethyl]-N-(1-propyl)-2-(1-pyrrolidinyl)cyclohexylamine.fumarate.H$_2$O | 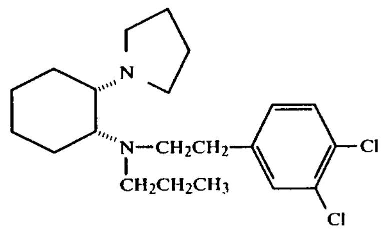 | C 58.03<br>H 7.35<br>N 5.41 | 58.03<br>7.06<br>5.66 | 169.5-170° C. | −11.1° C.<br>0.38, MeOH) | |

Biological Evaluation

Radioreceptor Assay

Compounds #1-3 were compared against di-o-tolyl-guanidine (DTG) [E. Weber et al, *Proc. Nat'l. Acad. Sci.*, 8784-8788, 1986] to determine the relative potency of the compounds interacting with the sigma receptor. To determine the effects of the compounds in a sigma receptor assay, crude membrane preparations were prepared as follows. Brains from male Sprague-Dawley rats were homogenized in 10 volumes (wt/vol) of 0.32 M sucrose, using a Polytron grinder. The homogenate was centrifuged at 900×G for 10 minutes at 4° C. The supernatant was collected and centrifuged at 22,000×g for 20 minutes at 4° C. The pellet was resuspended in 10 volumes of 50 mM Tris/HCl buffer (pH 7.4) and centrifuged at 22,000×g for 20 minutes at 4° C. The pellet was resuspended in 5 mM Tris/HCl buffer (pH 7.4) to give a final concentration of 250 mg/ml of the crude material. Incubation tubes were prepared in triplicate and contained 0.1 ml of tissue suspension, 2 nM of [$^3$H]-(+)-1-propyl-3-(3-hydroxyphenyl) piperidine {[$^3$H]-3-(+)-PPP}, and varying concentrations of the displacing ligand (0.1-1000 nM) in a final volume of 0.5 ml. After a 1 hr incubation at room temperature, the contents of the test tubes were filtered through GS filter paper which had been presoaked for at least 2 hours in 0.05% polyethyleneamine. The test tubes were rinsed three times with Tris/HCl buffer. Radioactivity on the filters was determined and IC$_{50}$ values were calculated from inhibition curves using the method of Cheng and Prusoff [*Biochem. Pharmacol.*, 22, 3099-3108, 1973].

TABLE II

| Test Compound | Ki apparent (nM) (units + SEM) |
| --- | --- |
| DTG | 47 ± 5 |
| Compound No. 1 | 230 ± 70 |
| Compound No. 2 | 30 ± 10 |
| Compound No. 3 | 20 ± 1 |

BLOCKAGE OF APOMORPHINE-INDUCED CLIMBING

Compounds of the invention were evaluated for their ability to block apomorphine-induced climbing. The evaluation of the compounds followed the method outlined by Protais [*Psychopharmacol.*, 50, 1-6, 1976]. Swiss-Webster mice, weighing 20-25 g, are pretreated with the compounds of the invention by i.p. or s.c. adiminstration at various times before 2 mg/kg apomorphine is administered s.c. in a volume of 1 ml/kg. All test compounds are administered in a volume of 10 ml/kg. Mice are rated at 10 and 20 minutes after apomorphine administration using the following rating scale: (0) forepaws on the floor, (1) forefeet holding the bars, and (2) four paws holding bars. Dose-response curves are analyzed by a computerized Finney assay [*Statistical Methods in Biological Assays*, 2nd Edn., Hatner Pub. Co., New York (1964)]. Compound No. 3 completely blocked apomorphine-induced climbing at a dose of 10 mg/kg.

Forebrain Ischemia Assay

Male Mongolian gerbils, 50-70 gm, were used as subjects. Compound No. 3 (50 mg/kg) was injected i.p. 30 minutes prior to carotid occlusion into 6 gerbils. In preparation for surgical procedures, the animals were lightly anesthetized with halothane and placed upside down on a heated pad with their snout within a nosecone. Nitrous oxide (70%): oxygen (30%) plus 0.5% halothane was circulated through the nosecone to provide continuous anesthesia throughout the surgical procedure. A midline incision was made in the neck and the carotid arteries were exposed. A length of suture thread was placed under each carotid. The thread was then tightened around each carotid and pressure applied to the thread to insure flow as occluded. Flow was occluded for 15 minutes and then the thread was removed. The carotids were visually inspected to confirm that reflow had occurred. The wound was then closed with autoclips and the gerbils allowed to recover. Following surgery, the gerbils were kept alive for 7 days. They were anesthetized with 100 mg/kg sodium pentobarbital and perfused transcardially with saline (with heparin) followed by buffered formalin. The brain was removed, trimmed and prepared for histological processing. Sections (10 microns) were stained with thionin. At 7 days following the ischemic insult, damaged neurons have been cleared away by glia and the extent of damage can be ascertained within the vulnerable CA1 region of the hippocampus. The degree of lesion in the CA1 region of the hippocampus was quantified by counting the pyramidal cell bodies in a 0.5 mm length of CA1 on the section corresponding to P 1.7 mm in the atlas of Loskota, Lomax and Verity [W. J. Loskota et al, *A Stereotaxic Atlas of the Mongolian Gerbil Brain*, Ann Arbor Science Publishers, Ann Arber, p. 77 (1974)]. The cell loss was significantly reduced in the gerbils given Compound No. 3 (p<0.01).

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical compositions may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may very widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound selected from
   (±)-cis-N-[2-(3,4-dichlorophenyl)ethyl]-N-methyl-2-(1-pyrrolidinyl)cyclohexylamine;
   1S,2S-(-)-cis-N-[2-(3,4-dichlorophenyl)ethyl]-N-methyl-2-(1-pyrrolidinyl) cyclohexylamine; and
   1R,2S-(+)-cis-N-[2-(3,4-dichlorophenyl)ethyl]-N-methyl-2-(1-pyrrolidinyl)cyclohexylamine;
   or a pharmaceutically acceptable salt thereof.

2. A pharmaceutical composition comprising a therapeutically effective amount of an active compound for treating or preventing a CNS-related disorder and a pharmaceutically-acceptable carrier or diluent, said active compound selected from a compound of claim 1.

3. A method for treating a patient afflicted with or susceptible to a CNS-related disorder, which method comprises administering to the patient a therapeutically-effective amount of a compound of claim 1.

* * * * *